US012051200B2

(12) United States Patent
Wang et al.

(10) Patent No.: US 12,051,200 B2
(45) Date of Patent: Jul. 30, 2024

(54) ARTIFICIAL INTELLIGENCE BASED MEDICAL IMAGE AUTOMATIC DIAGNOSIS SYSTEM AND METHOD (71) Applicant: NANJING TURING MICROBIAL TECHNOLOGIES CO. LTD, Jiangsu (CN)

(72) Inventors: Zhongxiao Wang, Jiangsu (CN); Wei Wu, Jiangsu (CN)

(73) Assignee: NANJING TURING MICROBIAL TECHNOLOGIES CO. LTD, Jiangsu (CN)

( * ) Notice: Subject to any disclaimer, the term of this patent is extended or adjusted under 35 U.S.C. 154(b) by 463 days.

(21) Appl. No.: 17/606,400

(22) PCT Filed: Apr. 24, 2020

(86) PCT No.: PCT/CN2020/086679
§ 371 (c)(1),
(2) Date: Oct. 25, 2021

(87) PCT Pub. No.: WO2020/216324
PCT Pub. Date: Oct. 29, 2020

(65) Prior Publication Data
US 2022/0198661 A1    Jun. 23, 2022

(30) Foreign Application Priority Data

Apr. 24, 2019 (CN) .......................... 201910334631.X (51) Int. Cl.
*G06T 7/00* (2017.01)
*G06V 10/26* (2022.01)
(Continued)

(52) U.S. Cl.
CPC ............ *G06T 7/0012* (2013.01); *G06V 10/26* (2022.01); *G06V 10/774* (2022.01);
(Continued)

(58) Field of Classification Search
CPC ......... G06T 7/0012; G06T 2207/10056; G06T 2207/20081; G06T 2207/20084;
(Continued)

(56) References Cited

U.S. PATENT DOCUMENTS 10,366,490 B2 *  7/2019 Xu .................... G06V 10/987
10,430,946 B1 * 10/2019 Zhou .................. A61B 5/02007
(Continued)

FOREIGN PATENT DOCUMENTS

CN          110895968 A      3/2020

OTHER PUBLICATIONS

Iakovidis, D.K. et al., Ratsnake:A Versatile Image Annotation Tool with Application to computer-Aided Diagnosis, Jan. 27, 2014, Hindawi Publishing corporation, The Scientific World Journal vol. 2014, pp. 1-12 (Year: 2014).*

*Primary Examiner* — Lewis G West
(74) *Attorney, Agent, or Firm* — Browdy and Neimark, PLLC (57) ABSTRACT An artificial intelligence (AI)-based medical image automatic diagnosis system and method. The method comprises: acquiring a medical microscope image and corresponding diagnostic data; annotating the medical microscope images to obtain annotation data corresponding to the medical microscope images; building a training set and a test set on the basis of the diagnostic data and annotation data corresponding to the medical microscope images; and performing training on the basis of a deep learning model to obtain the optimal AI classification model and the optimal AI semantic segmentation model to implement the automatic diagnosis of the medical microscope image of a test sample. The system and method can effectively save human resources, shorten the diagnosis time, and improve diagnosis accuracy.

20 Claims, 3 Drawing Sheets (51) Int. Cl.
*G06V 10/70* (2022.01)
*G06V 10/774* (2022.01)
*G06V 10/776* (2022.01)
*G06V 10/82* (2022.01)
*G06V 10/94* (2022.01)
*G06V 20/69* (2022.01)
*G16H 50/20* (2018.01)

(52) U.S. Cl.
CPC ............ *G06V 10/776* (2022.01); *G06V 10/82* (2022.01); *G06V 10/87* (2022.01); *G06V 10/95* (2022.01); *G06V 10/955* (2022.01); *G06V 20/695* (2022.01); *G06V 20/698* (2022.01); *G16H 50/20* (2018.01); *G06T 2207/10056* (2013.01); *G06T 2207/20081* (2013.01); *G06T 2207/20084* (2013.01); *G06V 2201/03* (2022.01)

(58) Field of Classification Search
CPC .......... G06T 2207/30024; G06V 10/26; G06V 10/774; G06V 10/776; G06V 10/82; G06V 10/87; G06V 10/95; G06V 10/955; G06V 20/695; G06V 20/698; G06V 2201/03; G16H 50/20; G16H 30/40; Y02A 90/10; G06N 3/045; G06N 3/0455
See application file for complete search history.

(56) References Cited

U.S. PATENT DOCUMENTS

| | | | | |
|---|---|---|---|---|
| 10,499,857 | B1* | 12/2019 | Nguyen | G06N 3/045 |
| 10,853,449 | B1* | 12/2020 | Nguyen | G16H 15/00 |
| 10,970,553 | B2* | 4/2021 | Zhang | G06V 20/41 |
| 11,556,746 | B1* | 1/2023 | Dasgupta | G06N 5/04 |
| 2020/0167930 | A1* | 5/2020 | Wang | G06N 3/08 |
| 2020/0211692 | A1* | 7/2020 | Kalafut | G06N 20/00 |
| 2020/0219262 | A1* | 7/2020 | Hsiao | G06V 10/764 |
| 2020/0258215 | A1* | 8/2020 | Kashyap | G06V 10/82 |
| 2020/0286614 | A1* | 9/2020 | Do | G06N 7/01 |

* cited by examiner

ARTIFICIAL INTELLIGENCE BASED MEDICAL IMAGE AUTOMATIC DIAGNOSIS SYSTEM AND METHOD

TECHNICAL FIELD

The present disclosure relates to the technical field of medical image processing, in particular, to an artificial intelligence-based medical image automatic diagnosis system and method.

BACKGROUND

Female reproductive tract infections are common diseases in female gynecology and represent a global social and public health problem. Bacterial vaginosis (BV) is the most common disease in female reproductive tract infections. In the normal vaginal flora, Lactobacilli dominate. *Lactobacillus* is a Gram-positive large and microaerobic *bacillus*, but grows better in an anaerobic environment. A coordinated and balanced state is maintained between the host and the flora, and among the flora. Bacterial vaginosis is likely to develop if the *Lactobacillus* population in the female vagina is greatly reduced and *Gardnerella vaginalis, Bacteroides* or small *Campylobacter* grows in large quantities. Clinically, the distribution density of *Lactobacillus, Gardnerella vaginalis, Bacteroides* and *Campylobacter* in the female vagina can be used to diagnose whether a patient has bacterial vaginosis. In medical technology, the microscopes image of vaginal secretions can be obtained through the Gram staining method, and the distribution of various bacteria in the female vagina can be obtained through the observation of the morphology and quantity of bacteria in the images, thereby diagnosing whether the patient has bacterial vaginosis.

This process of clinical diagnosis involves observing, processing, and analyzing numerous microscope images, which requires a lot of human resources and has high requirements for the professional knowledge and clinical experience of the medical staff. Therefore, there is a severe shortage of relevant inspection technicians at this stage.

With the development of artificial intelligence (AI) technology, significant progress has been made in current AI technology with regard to the field of natural image processing, such as image classification, recognition, and target detection. On this basis, researchers began to explore the application of AI technologies in the fields of medical image processing and auxiliary diagnosis and made certain progress in some respects, for example for the diagnosis of pathological images, CT images and fundus images, thus diagnosis level for applying AI and machine learning technologies has reached a relatively higher one. However, in the medical image diagnosis, the number of diseases processed through medical images is high and the degree of difference among various diseases is also great. Thus, for most diseases, it is still at the level of manual diagnosis process. In particular, the diagnosis of the gynecological microecological microscope images of the above-mentioned common gynecological diseases can currently only be performed manually, and there is no relevant intelligent diagnosis technology that can assist in diagnosis. Such manual diagnosis requires acquiring test samples from the patient, observing and analyzing the microscope images of the samples, and relying on the medical expertise of the inspectors to make a diagnosis, which requires a lot of human resources, and has low diagnosis efficiency and relatively low diagnosis accuracy rate.

SUMMARY

The present disclosure provides an artificial intelligence-based medical image automatic diagnosis system and a method to realize the automatic diagnosis of medical microscope images, save human resources, shorten the diagnosis time of diseases, and improve the diagnosis accuracy rate.

The first aspect of the present disclosure is to provide an artificial intelligence-based medical image automatic diagnosis system, including:

a data acquisition module, configured to acquire medical images and corresponding diagnostic data, and perform unified noise reduction and image enhancement processing on the medical images and the diagnostic data, wherein the medical images include medical microscope images;

a data annotation module, configured to annotate the image area where the pathogenic microorganisms in the medical images are located to form annotation data corresponding to the medical images;

a model training module, configured to, based on the deep learning model, train and obtain an AI classification model through a training set constructed from the medical images and the corresponding diagnostic data, and train and obtain an AI semantic segmentation model through a training set constructed from the medical images and the corresponding annotation data;

a model optimization module, configured to optimize the AI classification model through a test set constructed from the medical images and the corresponding diagnostic data, and optimize the AI semantic segmentation model through a test set constructed from the medical images and the corresponding annotation data, so as to train and obtain, by the model training module, an optimal AI classification model and an optimal AI semantic segmentation model; and a model deployment module, configured to perform application deployment on the optimal AI classification model and the optimal AI semantic segmentation model, both of which are used for providing automatic diagnosis of medical microscope images of test samples.

According to a preferred embodiment of the present disclosure, the application deployment of the optimal AI classification model and the optimal AI semantic segmentation model by the model deployment module includes: deploying the optimal AI classification model and the optimal AI semantic segmentation model to a server;

the system further includes an online diagnostic platform comprising a client and the server; and the server is configured to receive medical microscope images of test samples sent by the client, and output automatic diagnosis results of the medical microscope images.

According to a preferred embodiment of the present disclosure, the application deployment of the optimal AI classification model and the optimal AI semantic segmentation model by the model deployment module includes: deploying the optimal AI classification model and the optimal AI semantic segmentation model to an embedded chip;

the system further includes an embedded diagnostic platform comprising a microscope equipped with the embedded chip; and the microscope is configured to obtain the medical microscope images of the test samples and output the automatic diagnosis results of the medical microscope images through the processing by the embedded chip.

According to a preferred embodiment of the present disclosure, the medical microscope images include gynecological microecological microscope images.

According to a preferred embodiment of the present disclosure, the deep learning model includes a convolutional neural network model.

According to a preferred embodiment of the present disclosure, the optimization of the AI classification model and the AI semantic segmentation model by the model optimization module includes: selecting the inclination to high sensitivity or high specificity by adjusting the prediction probability thresholds of the AI classification model and the AI semantic segmentation model.

According to a preferred embodiment of the present disclosure, the diagnosis result includes the diagnosis of bacterial vaginosis.

According to a preferred embodiment of the present disclosure, the AI classification model includes a first classification model configured to output a first diagnosis result according to the medical microscope images of the test samples and a second classification model configured to output a second diagnosis result according to the medical microscope images of the test samples.

According to a preferred embodiment of the present disclosure, the convolutional neural network model is configured to calculate a loss function based on cross entropy, and the formula of the loss function is as follows:

$$J(\theta) = -\frac{1}{n}\sum_{j=1}^{n}\sum_{i=1}^{m} y_{ji}^{label} \log(y_{ji}^{prediction})$$

where m represents the number of classes, and n represents the batch size of the model; $y_{ji}^{label}$ represents the one-hot encoding vector of a label; $y_{ji}^{prediction} = f(\theta; x_j)$ represents a vector with elements that characterize the probabilities of the prediction result for each class, $x_j$ represents input data, and $\theta$ represents an updatable variable.

The second aspect of the present disclosure is to provide an artificial intelligence-based medical image automatic diagnosis method including:

acquiring medical images and corresponding diagnostic data, and performing unified noise reduction and image enhancement processing on the medical images and the diagnostic data, wherein the medical images include medical microscope images;

annotating the image area where the pathogenic microorganisms in the medical images are located to form annotation data corresponding to the medical images;

based on a deep learning model, training and obtaining an AI classification model through a training set constructed from the medical images and the corresponding diagnostic data, and training and obtaining an AI semantic segmentation model through a training set constructed from the medical images and the corresponding annotation data;

optimizing the AI classification model through a test set constructed from the medical images and the corresponding diagnostic data, and optimizing the AI semantic segmentation model through a test set constructed from the medical images and the corresponding annotation data, so as to train and obtain the optimal AI classification model and the optimal AI semantic segmentation model; and performing application deployment on the optimal AI classification model and the optimal AI semantic segmentation model, both of which are used for providing automatic diagnosis of the medical microscope images of the test samples.

According to a preferred embodiment of the present disclosure, the performing application deployment on the optimal AI classification model and the optimal AI semantic segmentation model includes: deploying the optimal AI classification model and the optimal AI semantic segmentation model to a server configured to receive the medical microscope images of the test samples sent by a client and output the automatic diagnosis results of the medical microscope images.

According to a preferred embodiment of the present disclosure, the performing application deployment on the optimal AI classification model and the optimal AI semantic segmentation model includes: deploying the optimal AI classification model and the optimal AI semantic segmentation model to an embedded chip installed in a microscope configured to obtain the medical microscope images of the test samples and output an automatic diagnosis result of the medical microscope images through the processing by the embedded chip.

According to a preferred embodiment of the present disclosure, the medical microscope images include gynecological microecological microscope images.

According to a preferred embodiment of the present disclosure, the deep learning model includes a convolutional neural network model.

According to a preferred embodiment of the present disclosure, the optimizing the AI classification model and the AI semantic segmentation model includes: selecting the inclination to high sensitivity or high specificity by adjusting the prediction probability thresholds of the AI classification model and the AI semantic segmentation model.

According to a preferred embodiment of the present disclosure, the diagnosis result includes the diagnosis of bacterial vaginosis.

According to a preferred embodiment of the present disclosure, the AI classification model includes a first classification model configured to output a first diagnosis result according to the medical microscope images of the test samples and a second classification model configured to output a second diagnosis result according to the medical microscope images of the test samples.

According to a preferred embodiment of the present disclosure, the convolutional neural network model is configured to calculate a loss function based on cross entropy, and the formula of the loss function is as follows:

$$J(\theta) = -\frac{1}{n}\sum_{j=1}^{n}\sum_{i=1}^{m} y_{ji}^{label} \log(y_{ji}^{prediction})$$

where m represents the number of classes, and n represents the batch size of the model; $y_{ji}^{label}$ represents the one-hot encoding vector of a label; $y_{ji}^{prediction} = f(\theta; x_j)$ represents a vector with elements that characterize the probabilities of the prediction result for each class, $x_j$ represents input data, and $\theta$ represents an updatable variable.

In the embodiments of the present disclosure, the optimal AI classification model and the optimal semantic segmentation model are obtained by training based on the deep learning model, and the automatic diagnosis of the medical microscope images of the test samples can be realized based on the application deployment of the optimal AI classification model and the optimal semantic segmentation model, which assists doctors in making treatment decisions, and can save a lot of human resources, shorten the diagnosis time of diseases, and improve the accuracy rate of diagnosis.

BRIEF DESCRIPTION OF THE DRAWINGS

To clearly illustrate technical solutions within the embodiments of the present disclosure or the prior art, the following will briefly introduce the drawings used in the description of technical solutions of the embodiments or the prior art. Obviously, the drawings in the following description are some embodiments of the present disclosure. For those of ordinary skill in the art, other drawings can be obtained based on these drawings without additional creative work.

DETAILED DESCRIPTION

In order to make the objectives, technical solutions, and advantages of the embodiments of the present disclosure clearer, the technical solutions in the embodiments of the present disclosure will be described clearly and completely in conjunction with the accompanying drawings in the embodiments of the present disclosure. Obviously, the described embodiments are parts of the embodiments of the present disclosure, rather than all the embodiments. Based on the embodiments in the present disclosure, all other embodiments obtained by those of ordinary skill in the art without creative work shall fall within the protection scope of the present disclosure.

In the present disclosure, it should be understood that terms such as "including" or "having" are intended to indicate the existence of the features, numbers, steps, actions, components, parts, or combinations thereof disclosed in this specification, and are not intended to exclude the possibility of existence or addition of one or more other features, numbers, steps, behaviors, components, parts or combinations thereof.

As mentioned earlier, in the existing medical image diagnosis, there is no automatic diagnosis technology for gynecological microecological microscope images. To this end, the embodiments of the present disclosure propose an artificial intelligence-based medical image automatic diagnosis system and a method.

Figure 1:
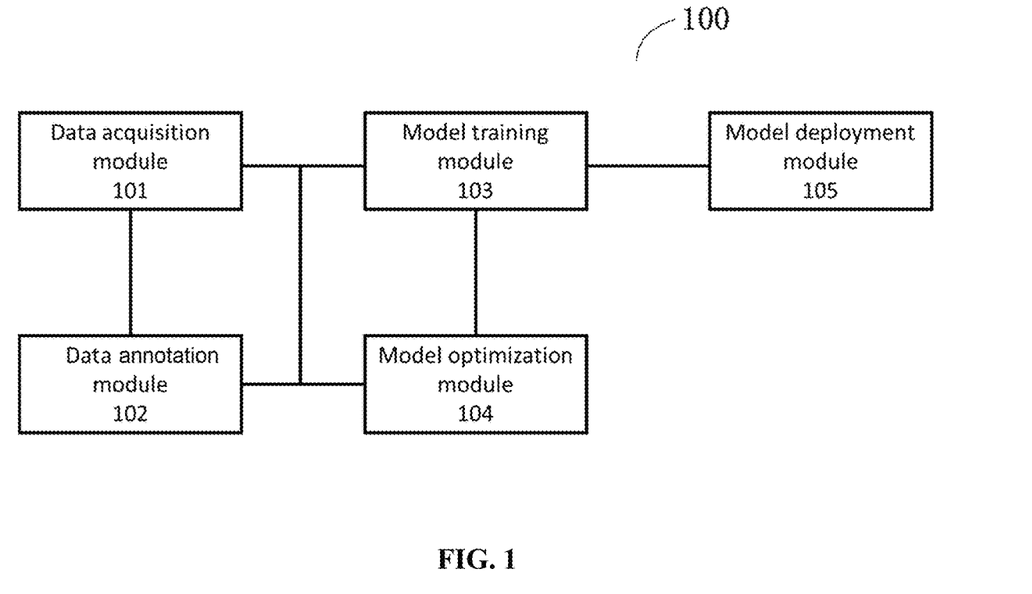
FIG. 1 is a schematic structural diagram of an artificial intelligence-based medical image automatic diagnosis system 100 according to a first embodiment of the present disclosure.

FIG. 1 is a schematic structural diagram of an artificial intelligence-based medical image automatic diagnosis system 100 according to a first embodiment of the present disclosure. The artificial intelligence-based medical image automatic diagnosis system 100 includes the following functional modules: a data acquisition module 101, a data annotation module 102, a model training module 103, a model optimization module 104, and a model deployment module 105.

The data acquisition module 101 is used to acquire medical images and corresponding diagnostic data, and perform unified noise reduction and image enhancement processing on the medical images and the diagnostic data.

Wherein, the medical images may include medical microscope images, and the diagnostic data may include a diagnosis result extracted from a diagnosis report made by a doctor on the medical microscope images. In some embodiments, the medical microscope images may include microscope images of a gynecological microecology test, including but not limited to microscope images of vaginal secretions used for the diagnosis of bacterial vaginosis.

The data annotation module 102 is used for annotating the image area where the pathogenic microorganisms in the medical images acquired by the data acquisition module 101 are located to form annotation data corresponding to the medical images.

In some embodiments, the pathogenic bacteria in the acquired microscope images can be annotated by a professional doctor, so as to extract the image area where the pathogenic bacteria are located to form the annotation data corresponding to the medical images.

The model training module 103 is used to based on a deep learning model, train through a training set constructed from the medical images and the corresponding diagnostic data to obtain an AI classification model, and train through a training set constructed from the medical images and the corresponding annotation data to obtain an AI semantic segmentation model.

In some embodiments, the deep learning model may include a convolutional neural network model. With deep learning technologies, the loss function and model parameters are further transformed and debugged through the convolutional neural network (CNN) that performs better in natural image processing, such as ResNet model, DenseNet model, Xception model, etc., thereby obtaining a deep learning model suitable for medical image processing. For the training of this deep learning model, further examples will be given later.

In the embodiment of the present disclosure, the medical images and the corresponding diagnostic data obtained by the data acquisition module 101, as well as the medical images and the corresponding annotation data obtained by the data annotation module 102 are uniformly divided into two parts, a training set and a test set. Among them, the training set of the medical images and the corresponding diagnostic data is used to train the AI classification model, the training set of the medical images and the corresponding annotation data is used to train the AI semantic segmentation model, and both test sets are used for performance testing and optimization of the training results of both models, respectively. The training data are input into the AI classification model and the AI semantic segmentation model, the back propagation algorithm is used to update the parameters of the AI classification model and the AI semantic segmentation model, so as to realize the training process of the AI classification model and the AI semantic segmentation model.

The AI semantic segmentation model trained based on the training set of medical images and corresponding annotation data, can automatically segment and identify the image area of pathogenic bacteria in the medical microscope images, and classify the pathogenic bacteria in the image area, and then provide diagnostic basis for the classification results of the medical microscope images; the AI classification model obtained by training through the medical images and the corresponding diagnostic data can classify the medical microscope images into the corresponding diagnosis results according to the distribution of the pathogenic bacteria obtained through semantic segmentation identification of the medical microscope images. On the other hand, the AI semantic segmentation model can also provide a basis for the interpretability of the AI classification model, and can help explain the reason why the AI classification model gives the corresponding diagnosis result to the medical microscope images.

The model optimization module 104 is used to optimize the AI classification model obtained by training through the model training module 103 using a test set constructed from the medical images and the corresponding diagnostic data, and optimize the AI semantic segmentation model obtained by training through the model training module 103 using a test set constructed from the medical images and the corresponding annotation data, so that the model training module 103 trains to obtain an optimal AI classification model and an optimal AI semantic segmentation model.

In some embodiments, the model optimization module 104 performs performance tests on the AI classification model through a test set constructed from the medical images and the corresponding diagnostic data, and performs performance tests on the AI semantic segmentation model through a test set constructed from the medical images and the corresponding annotation data, wherein the receiver characteristic curve (ROC) and the area(AUC) under the curve are mainly used to evaluate the performance of the tested AI classification model and AI semantic segmentation model. The closer the value of AUC is to 1, the better the performance of the model. At the same time, the model training module 103 can be guided according to the test results to select the hyperparameters in training the AI classification model and the AI semantic segmentation model, thereby forming a positive feedback mechanism for the training and optimization of the AI classification model and the AI semantic segmentation model. In clinical practice, generally more attention is paid to high sensitivity or high specificity. Sensitivity is defined as the probability of detecting positive among people who are diagnosed by the gold standard as being diseased (positive), also known as true positive; specificity is defined as the probability of detecting negative among people who are diagnosed by the gold standard as being non-diseased (negative), also known as true negative. The sensitivity or specificity close to 100% can be obtained by adjusting the prediction result probability thresholds of the AI classification model and the AI semantic segmentation model, while ensuring that the other index is higher than 75%.

The model deployment module 105 is used to perform application deployment to the optimal AI classification model and the optimal AI semantic segmentation model obtained by training through the model training module 103. The optimal AI classification model and the optimal AI semantic segmentation model after application deployment can provide automatic diagnosis of medical microscope images of test samples of patients.

In the embodiments of the present disclosure, the AI classification model and the AI semantic segmentation model are obtained by training through the AI deep learning model, which can realize automatic diagnosis of medical microscope images, and can assist doctors in making treatment decisions, save a lot of human resources, and improve the speed of disease diagnosis and the accuracy rate of diagnosis. At the same time, with the increases in the acquired medical microscope images and the data amount of corresponding diagnostic data, the AI classification model and the AI semantic segmentation model can also be continuously optimized.

In some specific embodiments, a ResNet18 convolutional neural network model is taken as an example to train an AI classification model for further description. The embodiment of the present disclosure calculates a loss function based on cross entropy, and the formula of the loss function is as follows:

$$J(\theta) = -\frac{1}{n}\sum_{j=1}^{n}\sum_{i=1}^{m} y_{ji}^{label}\log(y_{ji}^{prediction})$$

where m represents the number of classes, n represents the batch size; $y_{ji}^{label}$ is the one-hot encoding vector of a label, the vector is a binary vector with one bit being 1 and all other bits being 0. $y_{ji}^{prediction}=f(\theta; x_j)$, represents a vector with elements that characterize the probabilities of the prediction result for each class, the vector can be calculated by a softmax layer after the fully connection layer in the model, $x_j$ is input data, and $\theta$ is an updatable variable.

In the training process, the momentum optimization method can be used to optimize the model. The variable $\theta$ can be updated by the following formula:

$$v_t = \gamma v_{t-1} + \eta \nabla_\theta J(\theta)$$

$$\theta = \theta - v_t$$

where the value of y in the above formula can be 0.9, $\eta$ is the learning rate of the model, and t is the number of iterations. In one embodiment, in combination with the above formula, the variable $\theta$ can be updated based on the back propagation algorithm. In the inference process, the prediction result of the input data can be obtained from the position of the greatest element in the vector $y_{ji}^{prediction}$.

In some embodiments, considering that sensitivity is usually more important than specificity in clinical examinations, in order to improve the sensitivity of the diagnosis of bacterial vaginosis, a hierarchical model can be adopted in the AI classification model, that is, the AI classification model is divided into a first classification model and a second classification model. The Nugent scoring method, which is the gold standard for the diagnosis of bacterial vaginosis, is used as the diagnostic criteria. In the training process of the model, the first classification model is used to distinguish whether the patient's medical microscope images indicate bacterial vaginosis (Nugent score is 7-10 points) and other classes (Nugent score is 0-6 points), the second classification model is used to distinguish whether the patient's medical microscope images indicate normal state (Nugent score is 0-3 points) and intermediate state (Nugent score is 4-6 points). In the model inference process, the first classification model is used to classify the patient's medical microscope images into bacterial vaginosis (Nugent score is 7-10 points) and other classes (Nugent score is 0-6 points). When the classification result of the first classification model is other classes, the second classification model is used to further classify the other classes into the normal state and intermediate state.

This hierarchical model is more close to the actual requirements of clinical diagnosis than directly dividing the microscope images into the normal state, intermediate state and bacterial vaginosis (BV), because in clinical diagnosis, doctors pay more attention to distinguishing BV and other classes, therefore, the classification of the hierarchical model is utilized to prioritize the distinction between BV and other classes, and the normal state and intermediate state are then distinguished in other classes.

Figure 2:
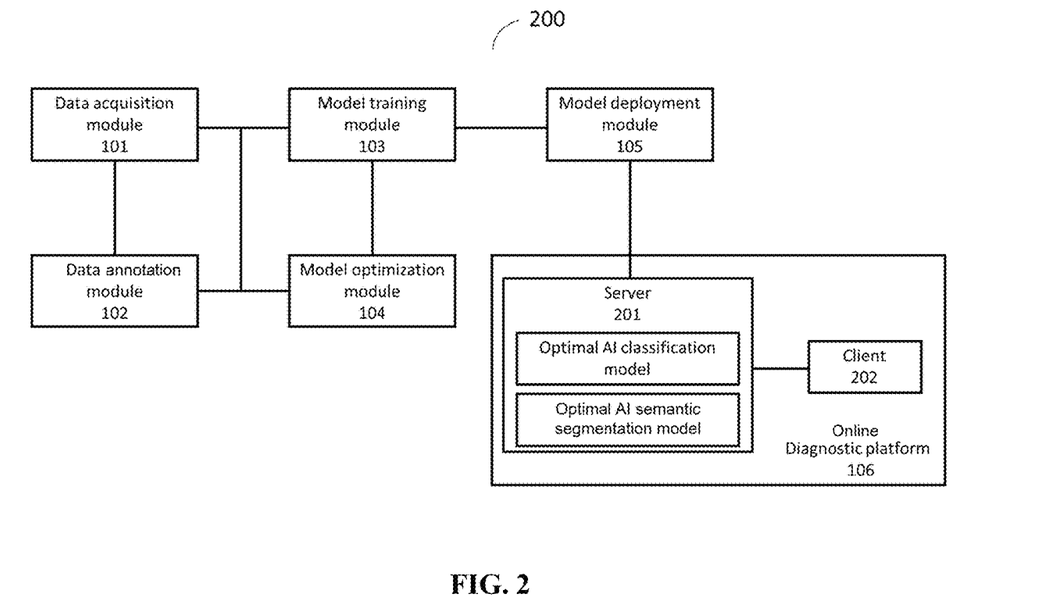
FIG. 2 is a schematic structural diagram of an artificial intelligence-based medical image automatic diagnosis system 200 according to a second embodiment of the present disclosure.

FIG. 2 is a schematic structural diagram of an artificial intelligence-based medical image automatic diagnosis system 200 according to a second embodiment of the present disclosure. The artificial intelligence-based medical image automatic diagnosis system 200 further includes an online diagnostic platform 106 on the basis of the embodiments shown in FIG. 1.

The online diagnostic platform 106 includes a server 201 and a client 202. Wherein, the model deployment module 105 is used to deploy the optimal AI classification model and the optimal AI semantic segmentation model obtained by training through the model training module 103 to the server 201. The server 201 receives the medical microscope images of the test samples sent by the client 202, and outputs the automatic diagnosis results of the medical microscope images.

In some embodiments, the server 201 may include a local network server or a cloud server. The client 202 may include, but is not limited to, a computer host, a portable computer, a tablet computer, a smart phone, and a medical testing device that can provide the reception and transmission of the medical microscope images.

In the embodiment of the present disclosure, the optimal AI classification model and the optimal AI semantic segmentation model are deployed to the online diagnostic platform, the client 202 can transmit the medical microscope images of the test samples to the server 201, and call the optimal AI classification model and the optimal AI semantic segmentation model in the server 201 for processing, so that the corresponding diagnosis conclusion can be drawn, and online automatic diagnosis can be realized. At the same time, the server 201 may also acquire image data misjudged by the AI model, and use the acquired image data to further train the iterative AI classification model and the AI semantic segmentation model.

Figure 3:
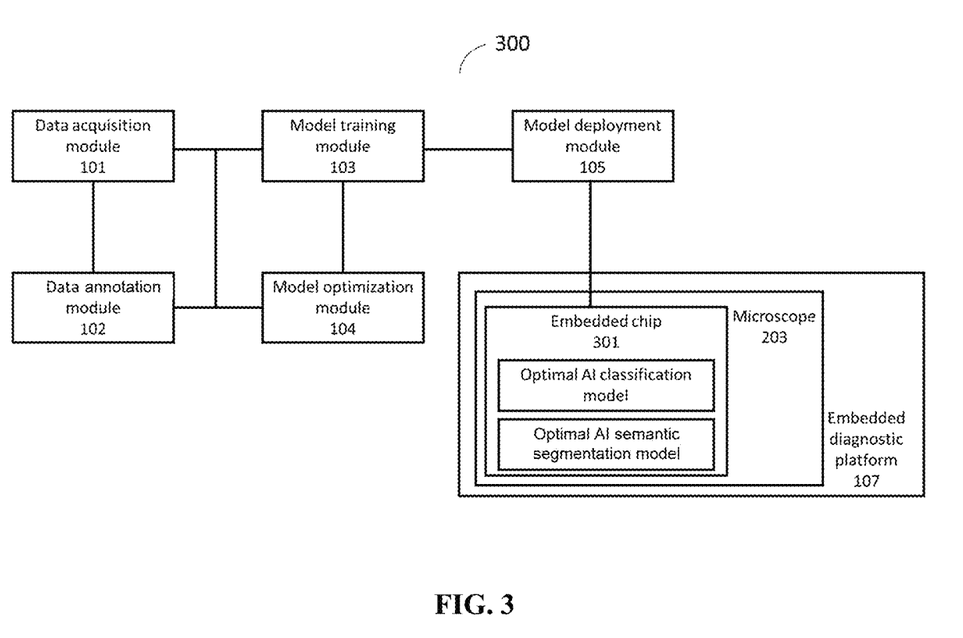
FIG. 3 is a schematic structural diagram of an artificial intelligence-based medical image automatic diagnosis system 300 according to a third embodiment of the present disclosure.

FIG. 3 is a schematic structural diagram of an artificial intelligence-based medical image automatic diagnosis system 300 according to a third embodiment of the present disclosure. The artificial intelligence-based medical image automatic diagnosis system 300 further includes an embedded diagnostic platform 107 on the basis of the embodiments shown in FIG. 1.

The embedded diagnostic platform 107 includes a microscope 203 equipped with an embedded chip 301. Wherein, the model deployment module 105 is used to deploy the optimal AI classification model and the optimal AI semantic segmentation model obtained by training through the model training module 103 to the embedded chip 301.

The microscope 203 is used to obtain the medical microscope images of the patient's test samples, and output the automatic diagnosis results of the medical microscope images through the processing by the embedded chip 301 installed.

In some embodiments, the microscope 203 may further include a communication interface (not shown in the drawings) for connecting to an external device. The communication interface may include a communication interface connected to a printing device, which is used to output the automatic diagnosis results of the medical microscope images detected by the microscope to the printing device for printing. The communication interface may also include a communication interface connected to a wired or wireless network, which is used to send the medical microscope images detected by the microscope and its automatic diagnosis results to a network storage unit for storage, or to a network display terminal for display.

In the embodiments of the present disclosure, the optimal AI classification model and the optimal AI semantic segmentation model are deployed to the embedded chip and integrated into the microscope for medical image detection, enabling primary hospitals to automatically run the AI automatic diagnosis system locally to serve patients without being connected to the network.

The artificial intelligence-based medical image automatic diagnosis system of the present disclosure can be applied to automatic diagnosis of common gynecological diseases such as female bacterial vaginosis, and has a high diagnosis speed and diagnosis accuracy rate. With the introduction of AI deep learning technologies, the diagnosis speed of the system is much faster than that of human. In the actual case test, the current diagnosis of female bacterial vaginosis has been excellent, and the AUC of the AI model on the test set can reach 0.986. In addition, as the trained AI classification model and AI semantic segmentation model can be copied quickly and in large quantities, it can solve the problem related to the lack of professional inspectors in a large number of primary hospitals by only training medical staff on simple AI system diagnosis operation procedures, without carrying out long-time professional skills training, so that a large number of primary hospitals have the capability to diagnose and treat common gynecological diseases such as female bacterial vaginosis, which also contributes to the country's hierarchical diagnosis and treatment system.

Figure 4:
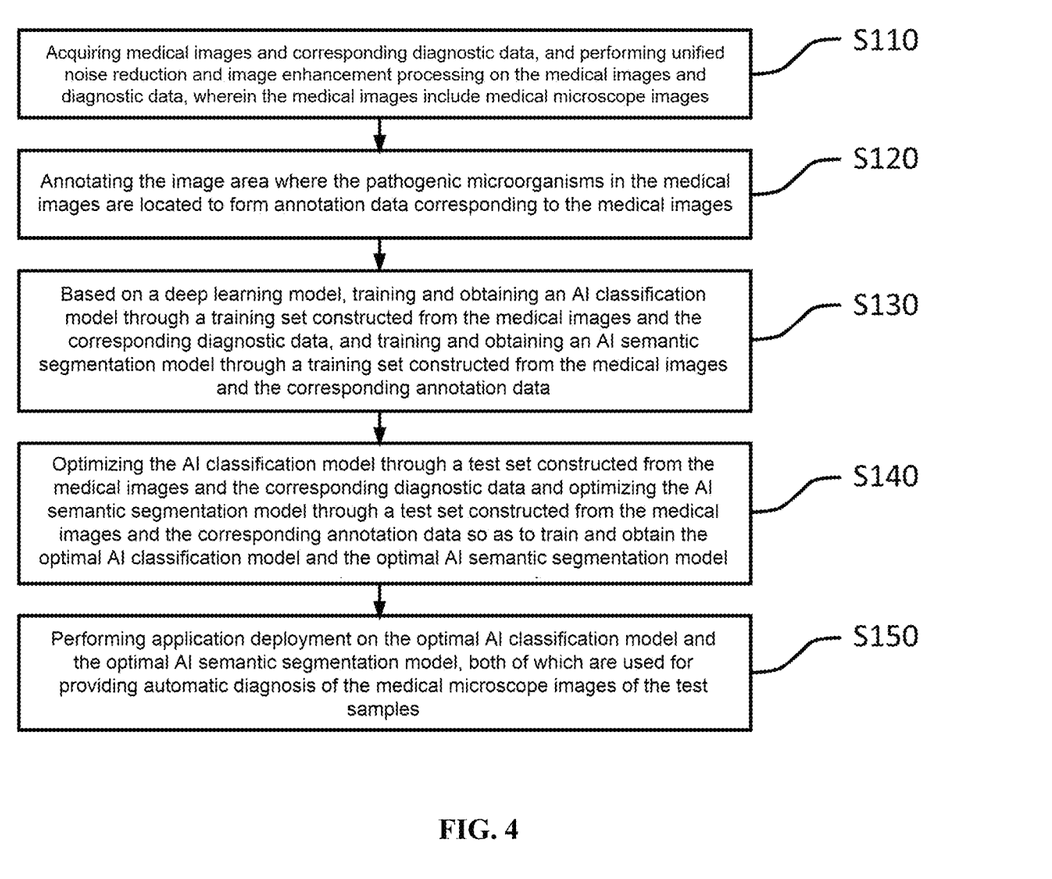
FIG. 4 is a schematic flowchart of an artificial intelligence-based medical image automatic diagnosis method according to an embodiment of the present disclosure.

FIG. 4 is a schematic flowchart of an artificial intelligence-based medical image automatic diagnosis method according to an embodiment of the present disclosure. As shown in FIG. 4, the artificial intelligence-based medical image automatic diagnosis method includes the following steps:

Step S110, acquiring medical images and corresponding diagnostic data, and performing unified noise reduction and image enhancement processing on the medical images and the diagnostic data;

Step S120, annotating the image area where the pathogenic microorganisms in the medical images are located to form annotation data corresponding to the medical images;

Step S130, based on a deep learning model, training through a training set constructed from the medical image and the corresponding diagnostic data to obtain an AI classification model, and training through a training set constructed from the medical image and the corresponding annotation data to obtain an AI semantic segmentation model;

Step S140, optimizing the AI classification model through a test set constructed from the medical image and the corresponding diagnostic data and optimizing the AI semantic segmentation model through a test set constructed from the medical image and the corresponding annotation data so as to train to obtain the optimal AI classification model and the optimal AI semantic segmentation model;

Step S150, performing application deployment to the optimal AI classification model and the optimal AI semantic segmentation model, both of which are used to provide automatic diagnosis of the medical microscope images of the test samples.

Wherein, in step S110, the medical images may include medical microscope images, and the diagnostic data may include a diagnosis result extracted from a diagnosis report made by a doctor on the medical microscope images. In some embodiments, the medical microscope images may include microscope images of a gynecological microecology test, including but not limited to the microscope images of vaginal secretions used for the diagnosis of bacterial vaginosis.

In some embodiments, step S120 includes annotating the pathogenic bacteria in the acquired microscope images by a professional doctor, so as to extract the image area where the pathogenic bacteria are located to form annotation data corresponding to the medical image.

In some embodiments, in step S130, the deep learning model may include a convolutional neural network model. With the deep learning technologies, the loss function and model parameters are further transformed and debugged through the convolutional neural network (CNN) that performs better in natural image processing, such as ResNet model, DenseNet model, Xception model, etc., thereby obtaining a deep learning model suitable for medical image processing.

In the embodiment of the present disclosure, the medical images and the corresponding diagnostic data acquired in step S110, and the medical images and the corresponding annotation data obtained in step S120 are uniformly divided into two parts, a training set and a test set; in step S130, the training set of the medical images and the corresponding diagnostic data is used to train the AI classification model, and the training set of the medical images and the corresponding annotation data is used to train the AI semantic segmentation model, both test sets are respectively used for performance testing and optimization of the training results of both models. The training data are input into the AI classification model and the AI semantic segmentation model, and the parameters of the AI classification model and the AI semantic segmentation model are updated through the back propagation algorithm, thereby realizing the training process of the AI classification model and the AI semantic segmentation model.

The AI semantic segmentation model trained based on the training set of the medical images and the corresponding annotation data, can automatically segment and identify the image area of pathogenic bacteria in the medical microscope images, and classify the pathogenic bacteria in the image area; the AI classification model obtained by training through the medical images and the corresponding diagnostic data can classify the medical microscope images into the corresponding diagnosis results according to the distribution of the pathogenic bacteria obtained through semantic segmentation identification of the medical microscope images.

In some embodiments, step S140 includes performing a performance test on the AI classification model through a test set constructed from the medical images and the corresponding diagnostic data, and performing a performance test on the AI semantic segmentation model through a test set constructed from the medical images and the corresponding annotation data, wherein the receiver characteristic curve (ROC) and the area (AUC) under the curve are mainly used to evaluate the performance of the tested AI classification model and AI semantic segmentation model. The closer the value of AUC is to 1, the better the performance of the model. At the same time, the model training module 103 can be guided according to the test results to select the hyperparameters in training the AI classification model and the AI semantic segmentation model, thereby forming a positive feedback mechanism for the training and optimization of the AI classification model and the AI semantic segmentation model. In clinical practice, more attention is paid to high sensitivity or high specificity. Sensitivity is defined as the probability of detecting positive among people who are diagnosed by the gold standard as being diseased (positive), also known as true positive; specificity is defined as the probability of detecting negative among people who are diagnosed by the gold standard as being non-diseased (negative), also known as true negative. The sensitivity or specificity close to 100% can be obtained by adjusting the prediction result probability threshold of the AI classification model and the AI semantic segmentation model, while ensuring that the other index is higher than 75%.

In some specific implementation manners, for training the AI classification model through the ResNet18 convolutional neural network model, refer to the description of the foregoing embodiments, which will not be repeated here.

In some embodiments, in step S150, the application deployment of the optimal AI classification model and the optimal AI semantic segmentation model includes deploying the optimal AI classification model and the optimal AI semantic segmentation model to a server. The server can receive the medical microscope images of the test samples sent by a client, and output the automatic diagnosis results of the medical microscope images.

In some embodiments, the server may include a local network server or a cloud server. The client may include, but is not limited to, a computer host, a portable computer, a tablet computer, a smart phone, and a medical testing device that can provide the reception and transmission of the medical microscope images.

In some embodiments, in step S150, the application deployment of the optimal AI classification model and the optimal AI semantic segmentation model includes deploying the optimal AI classification model and the optimal AI semantic segmentation model to an embedded chip. The embedded chip can be installed in a microscope which is used to obtain the medical microscope images of the test samples, and output the automatic diagnosis results of the medical microscope images through the processing by the embedded chip.

In some embodiments, the microscope may further include a communication interface for connecting an external device. The communication interface may include a communication interface connected to a printing device, which is used to output the automatic diagnosis results of the medical microscope images detected by the microscope to the printing device for printing. The communication interface may also include a communication interface connected to a wired or wireless network, which is used to send the medical microscope images detected by the microscope and its automatic diagnosis results to a network storage unit for storage, or to a network display terminal for display.

The artificial intelligence-based medical image automatic diagnosis method of the present disclosure can be applied to automatic diagnosis of common gynecological diseases such as female bacterial vaginosis, and has a high diagnosis speed and diagnosis accuracy rate. With the introduction of AI deep learning technologies, the diagnosis speed of this method is much faster than that of human. After testing in actual cases, the current diagnosis of female bacterial vaginosis has been excellent, and the AUC of the AI model on the test set can reach 0.986. In addition, as the trained AI classification model and AI semantic segmentation model can be copied quickly and in large quantities, it can solve the problem related to the lack of professional inspectors in a large number of primary hospitals by only training medical staff on simple AI system diagnostic operation procedures, without carrying out long-time professional skill training, so that a large number of primary hospitals have the capability to diagnose and treat common gynecological diseases such as female bacterial vaginosis, which also contributes to the country's hierarchical diagnosis and treatment system.

Finally, it should be noted that the above embodiments are only used to illustrate the technical solutions of the present disclosure, not to limit them; although the present disclosure has been described in detail with reference to the foregoing embodiments, those of ordinary skill in the art should understand: it is still possible to modify the technical solutions described in the foregoing embodiments, or equivalently replace some or all of the technical features; however, these modifications or replacements do not cause the essence of the corresponding technical solutions to deviate from the scope of the technical solutions of the embodiments of the present disclosure.

What is claimed is:

1. An artificial intelligence-based medical image automatic diagnosis system comprising:
   a data acquisition module, configured to acquire medical images and corresponding diagnostic data and perform unified noise reduction and image enhancement processing on the medical images and the diagnostic data, wherein the medical images include medical microscope images;
   a data annotation module, configured to annotate the image area where the pathogenic microorganisms in the medical images are located to form annotation data corresponding to the medical images;
   a model training module, configured to, based on a deep learning model, train and obtain an AI classification model through a training set constructed from the medical images and the corresponding diagnostic data, and train and obtain an AI semantic segmentation model through a training set constructed from the medical images and corresponding annotation data;
   a model optimization module, configured to optimize the AI classification model through a test set constructed from the medical images and the corresponding diagnostic data and optimize the AI semantic segmentation model through a test set constructed from the medical images and the corresponding annotation data, so as to train and obtain, from the model training module, an optimal AI classification model and an optimal AI semantic segmentation model; and
   a model deployment module, configured to perform application deployment on the optimal AI classification model and the optimal AI semantic segmentation model, both of which are used for providing automatic diagnosis of the medical microscope images of test samples.

2. The artificial intelligence-based medical image automatic diagnosis system according to claim 1, wherein the model deployment module is further configured to deploy the optimal AI classification model and the optimal AI semantic segmentation model to a server;
   the system further comprises an online diagnostic platform comprising a client and the server; and
   the server is configured to receive the medical microscope images of the test samples sent by the client and output an automatic diagnosis result of the medical microscope images.

3. The artificial intelligence-based medical image automatic diagnosis system according to claim 2, wherein the medical microscope images comprise gynecological microecological microscope images and the diagnosis result includes the diagnosis of bacterial vaginosis.

4. The artificial intelligence-based medical image automatic diagnosis system according to claim 3, wherein the AI classification model includes a first classification model configured to output a first diagnosis result according to the medical microscope images of the test samples and a second classification model configured to output a second diagnosis result according to the medical microscope images of the test samples.

5. The artificial intelligence-based medical image automatic diagnosis system according to claim 1, wherein the model deployment module is further configured to deploy the optimal AI classification model and the optimal AI semantic segmentation model to an embedded chip;
   the system further comprises an embedded diagnostic platform comprising a microscope installed with the embedded chip; and
   the microscope is configured to obtain the medical microscope images of the test samples and output an automatic diagnosis result of the medical microscope images through the processing by the embedded chip.

6. The artificial intelligence-based medical image automatic diagnosis system according to claim 5, wherein the medical microscope images comprise gynecological microecological microscope images and the diagnosis result includes the diagnosis of bacterial vaginosis.

7. The artificial intelligence-based medical image automatic diagnosis system according to claim 6, wherein the AI classification model includes a first classification model configured to output a first diagnosis result according to the medical microscope images of the test samples and a second classification model configured to output a second diagnosis result according to the medical microscope images of the test samples.

8. The artificial intelligence-based medical image automatic diagnosis system according to claim 1, wherein the deep learning model comprises a convolutional neural network model.

9. The artificial intelligence-based medical image automatic diagnosis system according to claim 8, wherein the model optimization module is further configured to select the inclination to high sensitivity or high specificity by adjusting the prediction probability thresholds of the AI classification model and the AI semantic segmentation model.

10. The artificial intelligence-based medical image automatic diagnosis system according to claim 8, wherein the convolutional neural network model is configured to calculate a loss function based on cross entropy, and the formula of the loss function is as follows:

$$J(\theta) = -\frac{1}{n}\sum_{j=1}^{n}\sum_{i=1}^{m} y_{ji}^{label} \log\left(y_{ji}^{prediction}\right)$$

where m represents the number of classes, and n represents the batch size of the model; $y_{ji}^{label}$ represents the one-hot encoding vector of a label; $y_{ji}^{prediction} = f(\theta; x_j)$, represents a vector with elements that characterize the probabilities of the prediction result for each class, $x_j$ represents input data, and $\theta$ represents an updatable variable.

11. An artificial intelligence-based medical image automatic diagnosis method, comprising:
   acquiring medical images and corresponding diagnostic data and performing unified noise reduction and image enhancement processing on the medical images and the diagnostic data, wherein the medical images include medical microscope images;
   annotating the image area where the pathogenic microorganisms in the medical images are located to form annotation data corresponding to the medical images;
   based on a deep learning model, training and obtaining an AI classification model through a training set constructed from the medical images and the corresponding diagnostic data, and training and obtaining an AI semantic segmentation model through a training set constructed from the medical images and the corresponding annotation data;
   optimizing the AI classification model through a test set constructed from the medical images and the corresponding diagnostic data and optimizing the AI semantic segmentation model through a test set constructed from the medical images and the corresponding annotation data, so as to train and obtain an optimal AI classification model and an optimal AI semantic segmentation model; and
   performing application deployment on the optimal AI classification model and the optimal AI semantic segmentation model, both of which are used for providing automatic diagnosis of the medical microscope images of the test samples.

12. The artificial intelligence-based medical image automatic diagnosis method according to claim 11, wherein the performing application deployment on the optimal AI classification model and the optimal AI semantic segmentation model comprises: deploying the optimal AI classification model and the optimal AI semantic segmentation model to a server configured to receive the medical microscope images of the test samples sent by a client and output the automatic diagnosis result of the medical microscope images.

13. The artificial intelligence-based medical image automatic diagnosis method according to claim 12, wherein the medical microscope images comprise gynecological microecological microscope images and the diagnosis result includes the diagnosis of bacterial vaginosis.

14. The artificial intelligence-based medical image automatic diagnosis method according to claim 13, wherein the AI classification model comprises a first classification model configured to output a first diagnosis result according to the medical microscope images of the test samples and a second classification model configured to output a second diagnosis result according to the medical microscope images of the test samples.

15. The artificial intelligence-based medical image automatic diagnosis method according to claim 11, wherein the performing application deployment on the optimal AI classification model and the optimal AI semantic segmentation model comprises: deploying the optimal AI classification model and the optimal AI semantic segmentation model to an embedded chip installed in a microscope configured to obtain the medical microscope images of the test samples and output an automatic diagnosis result of the medical microscope images through the processing by the embedded chip.

16. The artificial intelligence-based medical image automatic diagnosis method according to claim 15, wherein the medical microscope images comprise gynecological microecological microscope images and the diagnosis result includes the diagnosis of bacterial vaginosis.

17. The artificial intelligence-based medical image automatic diagnosis method according to claim 16, wherein the AI classification model comprises a first classification model configured to output a first diagnosis result according to the medical microscope images of the test samples and a second classification model configured to output a second diagnosis result according to the medical microscope images of the test samples.

18. The artificial intelligence-based medical image automatic diagnosis method according to claim 11, wherein the deep learning model comprises a convolutional neural network model.

19. The artificial intelligence-based medical image automatic diagnosis method according to claim 18, wherein the optimizing the AI classification model and the AI semantic segmentation model comprises: selecting the inclination to high sensitivity or high specificity by adjusting the prediction probability thresholds of the AI classification model and the AI semantic segmentation model.

20. The artificial intelligence-based medical image automatic diagnosis method according to claim 18, wherein the convolutional neural network model is configured to calculate a loss function based on cross entropy, and the formula of the loss function is as follows:

$$J(\theta) = -\frac{1}{n}\sum_{j=1}^{n}\sum_{i=1}^{m} y_{ji}^{label} \log\left(y_{ji}^{prediction}\right)$$

where m represents the number of classes, and n represents the batch size of the model; $y_{ji}^{label}$ represents the one-hot encoding vector of a label; $y_{ji}^{prediction} = f(\theta; x_j)$, represents a vector with elements that characterize the probabilities of the prediction result for each class, $x_j$ represents input data, and $\theta$ represents an updatable variable.

* * * * *